United States Patent [19]

Parker

[11] Patent Number: 4,827,938

[45] Date of Patent: * May 9, 1989

[54] TWO-BAND OPTICAL COMPARATOR FOR USE WITH CHOPPED CW SINGLET OXYGEN MONITOR

[75] Inventor: John G. Parker, Olney, Md.

[73] Assignee: The Johns Hopkins University, Baltimore, Md.

[*] Notice: The portion of the term of this patent subsequent to Mar. 18, 2003 has been disclaimed.

[21] Appl. No.: 230,706

[22] Filed: Aug. 9, 1988

Related U.S. Application Data

[63] Continuation of Ser. No. 865,315, May 21, 1986, abandoned.

[51] Int. Cl.$^4$ .......................... A61B 6/00; A61N 5/00
[52] U.S. Cl. ..................................... 128/633; 128/634; 128/654; 128/664; 128/362
[58] Field of Search ................................ 128/633–635, 128/654, 664, 665, 395–398, 362, 303.1

[56] References Cited

U.S. PATENT DOCUMENTS 4,576,173 3/1986 Parker et al. ....................... 128/633

Primary Examiner—Kyle L. Howell
Assistant Examiner—John C. Hanley
Attorney, Agent, or Firm—Robert E. Archibald; Howard W. Califano

[57] ABSTRACT

An improved apparatus and method for detecting singlet oxygen emission produced during photoradiation is disclosed. The invention utilizes a two-band optical comparator to detect optical emissions. The optical comparator comprises an in-band filter that passes light in the 1270 nm singlet oxygen emission band and an out-of-band filter that passes light outside of the 1270 nm singlet oxygen emission band. The signal detected when the out-of-band filter is used is composed essentially of a fluorescence emission. This detected signal is used to synchronize an electronic reference signal. The electronic reference signal is used by a signal processing means to isolate a phase delayed singlet oxygen emission component which appears with a fluorescence emission component in the 1270 nm singlet oxygen emission band.

8 Claims, 3 Drawing Sheets

TWO-BAND OPTICAL COMPARATOR FOR USE WITH CHOPPED CW SINGLET OXYGEN MONITOR

STATEMENT OF GOVERNMENTAL INTEREST

The Government has rights in this invention pursuant to Contract No. N00024-85-C-5301 awarded by the Department of the Navy.

"This is a continuation of co-pending application Ser. No. 865,315 filed on May 21, 1986 now abandoned."

BACKGROUND OF THE INVENTION

1. Field of the Invention

This invention relates to an improved method and apparatus for detecting the singlet oxygen emission produced during photoradiation when a chopped source of optical radiation is used to excite a photodynamic sensitizer.

2. Description of Prior or Contemporary Art

When certain non-toxic photodynamic sensitizers, such as hematoporphyrin derivative (HPD) and components thereof, are injected intravenously into the human body, they are selectively retained by cancerous tissue. Thus, two or three days after injection, significantly higher levels of the photodynamic sensitizer are retained in malignant tissue. The tumor is then exposed to a therapeutic light and this light energy causes the photodynamic sensitizer to be excited to an energetic metastable triplet state. Through a direct intermolecular process, the sensitizer transfers this energy to oxygen molecules present in the tissue and raises them from the ground triplet to the first excited electronic singlet state, $^1O_2$ [symbolic designation of molecular oxygen in the $^1\Delta g$ electronic state]. The singlet oxygen, $^1O_2$, attacks and functionally destroys vital cellular components ultimately inducing necrosis and destroying the cancerous tissue. The advances and problems associated with this cancer treatment are addressed in an article by Thomas J. Dougherty et al entitled "Photoradiation Therapy for the Treatment of Malignant Tumors" published in *Cancer Research*, Vol. 38, pages 2628–2635 (1978).

SUMMARY OF THE INVENTION

The present invention represents an improvement to the singlet oxygen monitoring apparatus and method described by John G. Parker and William D. Stanbro in U.S. Pat. No. 4,576,173, entitled "Electro-Optical Device and Method for Monitoring Instantaneous Singlet Oxygen Contraction Produced During Photoradiation Using a CW Excitation Source". The present Applicant discovered that a phase shift introduced by the photodetector and associated electronics reduced the sensitivity of the aforementioned singlet oxygen monitoring apparatus.

The present invention utilizes a two band optical comparator apparatus and method to compensate for this undesirable phase shift. The invention utilizes an out-of-band filter that passes a first band of light adjacent to the singlet oxygen 1270 nm emission band and, an in-band filter that passes a second band essentially comprising the singlet oxygen 1270 nm emission band. Optical emission in said first band is essentially composed of a fluorescence emission signal; and optical emissions in said second band comprises a fluorescence emission component and a singlet oxygen emission component that is delayed in time with respect to such fluorescence emission component. With the first band located spectrally near the second band, any phase difference between the fluorescence emission signal detected in said first band and the fluorescence emission component detected in the second band is minimal.

To compensate for the undesirable phase error an electrical reference signal is synchronized with the detected signal from the first band, which is essentially composed of the fluorescence emission signal. This electrical reference signal is then used by the signal processing apparatus to separate the composite electrical signal detected in the second band into the fluorescence emission component and the singlet oxygen emission component. Separation of these two components is possible because a component of the composite electrical signal 90° out of phase from said electrical reference signal will indicate the singlet oxygen emission component.

DESCRIPTION OF THE PREFERRED EMBODIMENTS

Photodynamic therapy involves injecting a patient with a photodynamic sensitizer, such as hematoporphyrin derivative, and after the sensitizer has localized at the appropriate biological site, illuminating that site with optical energy. The resulting photodynamic action causes singlet oxygen to be generated. When the singlet oxygen interacts with molecules at the biological site, a relatively weak collisionally induced emission occurs at the singlet oxygen 1270 nm emission band. (The singlet oxygen emission band is centered at 1270 nm and has a full-width-at-half-maximum (FWHM) of 0.02 micron extending from 1260 nm to 12 80 nm. This band shall hereafter be referred to as the singlet oxygen 1270 nm emission band or 1270 nm band).

Figure 1:
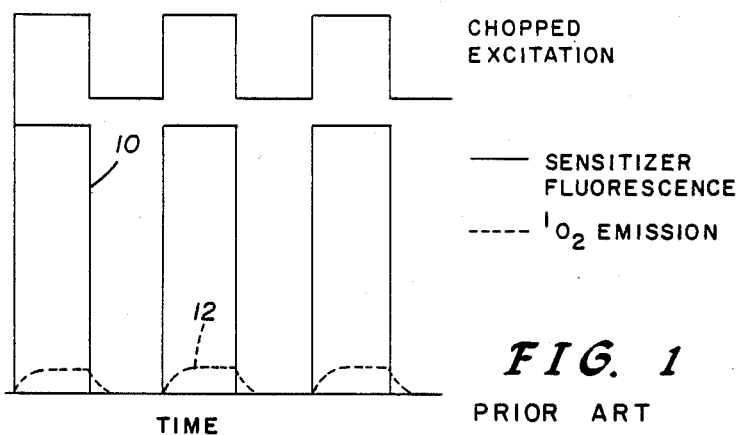
FIG. 1 is graph showing the composite fluorescence/singlet oxygen emission signals appearing in the 1270 nm band.

By optically detecting and monitoring this emission it is possible to determine the instantaneous rate at which singlet oxygen is being generated and is attacking biological matter. However, as illustrated in FIG. 1, the optical energy emitted in the 1270 nm band during photodynamic therapy is a composite signal comprising a first component 10 due to the spectrally diffuse fluorescence of the sensitizer and auto-fluorescence of the biological matter and, a second component 12 produced by the emission from singlet oxygen molecules. Both the first component fluorescence signal 10 and the singlet oxygen emission 12 arise as a consequence of optical excitation of the sensitizer and both are inextricably intertwined in the 1270 nm band. There is no way of spectrally separating the singlet oxygen emissions 12 from the fluorescence component 10 both appearing in the 1270 nm singlet oxygen emission band. The fluorescence component 10 in the 1270 nm band also is generally much larger in magnitude than the relatively weak singlet oxygen emissions 12. The central difficulty to be overcome, therefore, in monitoring the singlet oxygen emission is to separate the singlet oxygen emission component from the fluorescence component.

Figure 2:
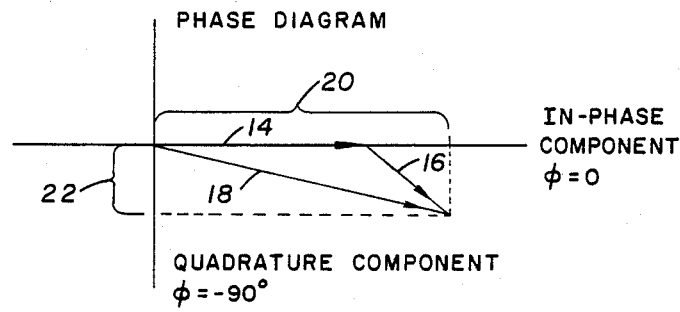
FIG. 2 is a phase diagram of the composite fluorescence/singlet oxygen emission signal appearing in the 1270 nm band.

In U.S. Pat. No. 4,576,173, which is incorporated herein by reference, the present Applicant along with William D. Stanbro disclosed an invented method and apparatus for separating the singlet oxygen emission signal from the composite signal. That invention was based upon the fact that the fluorescence component occurs simultaneously with the excited light but the singlet oxygen emission component is delayed in time with respect to the fluorescence component. This time delay is due to the fact that formation of the singlet oxygen is not directly coupled to the optical excitation. Formation of singlet oxygen involves a collisional transfer of energy from the sensitizer metastable triplet state, thus delayed with respect to the initiation of the optical excitation by the time required to bring about collision of the ground electronic state dissolved oxygen $^3O_2$ with the excited sensitizer. FIG. 2 contains a phase diagram showing the phase relationship between the fluorescence component and the singlet oxygen emission component of the composite optical signal. The horizontal axis of the phase diagram shows the in-phase or real component (phase $\phi=0°$) and the vertical axis shows the quadrature or imaginary component (phase angle $\phi=-90°$). Since the fluorescence component (14) is essentially concurrent with the excitation light, its phase vector will appear at phase angle $\phi=0°$ (e.g., the fluorescence component is in-phase with the chopped CW excitation signal). However, the singlet oxygen emission signal, as shown in the above equations, appears as a vector (16) having a phase delay (e.g., the singlet oxygen emission signal lags the fluorescence component (14). The sum of the fluorescence component vector 14 and the singlet oxygen emission vector 16 produces a resultant signal vector 18. The resultant signal vector can be divided into a real component (phase angle $\phi=0°$) 20 and a quadrature component (phase angle $\phi=-90°$) 22. The real or in-phase component is the sum of the real sensitizer fluorescence component and the real singlet oxygen emission component. However, the imaginary or quadrature component 22 is only dependent on singlet oxygen emission.

Figure 3:
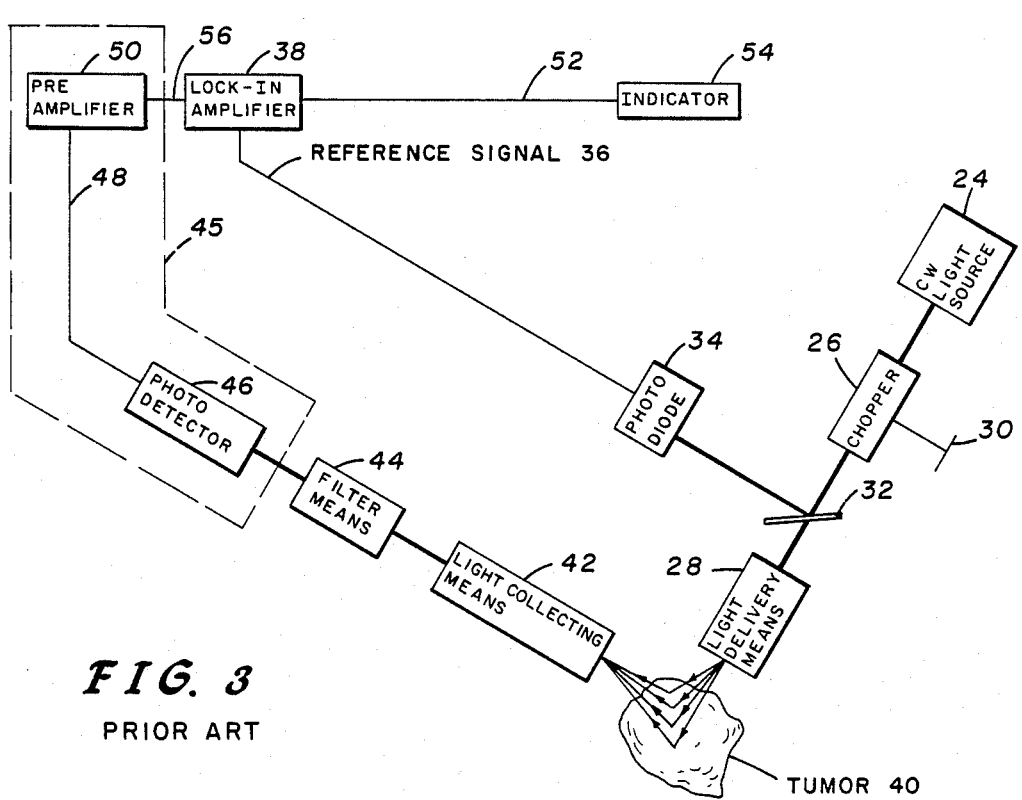
FIG. 3 illustrates, in block diagrammatic form, an apparatus used to process the composite fluorescence/singlet oxygen emission signal so as to extract the singlet oxygen emission signal.

FIG. 3 is a block diagrammatic view of the apparatus used to separate and detect the singlet oxygen component as taught by the above-referenced patent (U.S. Pat. No. 4,576,173). A CW light source 24, which may be a laser is chopped by chopper 26 and directed by a light delivery means 28 onto the biological mass 40. The chopper may be a mechanical chopper, an acousto-optic modulator, or similar devices capable of chopping the excitation beam at a rate from 1 kHz to 100 kHz or higher. The chopper 26 has adjustment 30 so that the chopping frequency ($f_c$) can be set at particular values or scanned across a range of values. The light delivery means 28 used to direct the chopped CW excitation beam can be a lens arrangement or a fiberoptic link. A beam splitter 32 and a photodiode 34 work in conjunction to produce an electrical reference signal 36, which is used to synchronize the lock-in amplifier 38. Alternatively, an electrical signal produced directly by the chopping circuit or by a timing circuit can act as a reference signal 36, to synchronize the lock-in amplifier. The biological mass or tumor 40 which has absorbed a photodynamic sensitizer, such as hematoporphyrin derivative or components thereof, and which is optically irradiated emits a composite signal composed of a fluorescence component and a singlet oxygen emission component. A light collecting means 42, which may be a lens arrangement or fiberoptic link, collects the light. The collected light is then filtered by filter means 44 which passes light in the singlet oxygen 1270 nm emission band. The filtered light is then directed to a photo detector 46 which converts the composite fluorescence/singlet oxygen emission signal, both appearing in 1270 nm emission band, into an electrical signal 48. The electrical signal 48 is amplified by preamplifier 50; photodetector 46 and preamplifier 50 together forming an electro-optical means 45 for detecting optical emissions. The output of the preamplifier 50 is fed to lock-in amplifier 38. The inventors have used an EG&G PAR Model 124A lock-in amplifier, but other known lock-in amplifiers or synchronous detectors can be used as well. The lock-in amplifier 38 has as input the reference signal 36 and the output from preamplifier 50. The imaginary or quadrature component (phase angle $\phi=-90°$) of the composite signal is processed by the lock-in amplifier 52. Indicator 54 connects to output terminal 52 and displays the magnitude of the processed signal which is directly proportional to the magnitude of the instantaneous singlet oxygen concentration generated in the biological mass 40 by photoradiation.

Figure 4:
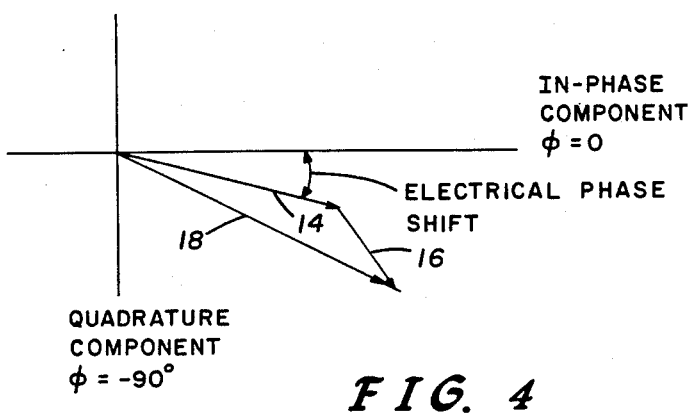
FIG. 4 is a phase diagram of the composite fluorescence/singlet oxygen emission signal appearing in the 1270 nm band that illustrates the undesired electrical phase shift.

The present invention represents an improvement to the apparatus shown in FIG. 3 and claimed in U.S. Pat. No. 4,576,173. Applicant discovered that a small phase shift was occurring between the electrical composite signal 56 from the detector/preamplifier and the reference electrical signal 36. The phase relationship between the fluorescence component vector 14 and the singlet oxygen emission vector 16, as shown in FIG. 2, was maintained. However, if the horizontal axis is synchronized with the reference electrical signal 36, the additional phase delay would cause vectors 14, 16, and 18 to appear rotated from the horizontal axis. A graphic representation of this rotation caused by the additional phase shift in the electrical signal appears in FIG. 4. As a result, the quadrature electrical component ($\phi=90°$) would include a small component of the fluorescence signal component, which would introduce an error in the singlet oxygen measurement. (Note: In a biological medium the fluorescence component vector 14 is many times larger than the singlet oxygen emission vector 16. Therefore, any slight rotation of the fluorescence component vector from the horizontal axis will produce a component along the quadrature axis that may mask the singlet oxygen quadrature signal.)

Applicant believes this phase shift is an electronic phase shift that occurs in the detector 46 and preamplifier 50. It is believed that the electronic circuit in the preamplifier adds a phase delay. It is also believed that a phase shift occurs in the detector. The phase shift occurring in the photodetector appears to vary with wavelength. Therefore, the photodetector will, for instance, introduce a different phase shift for the excitation wavelength as it would for optical radiation in the singlet oxygen 1270 nm emission band. Further, Applicant believes that the electrical phase shift changes as a function of a change in intensity of the received optical radiation.

Figure 5:
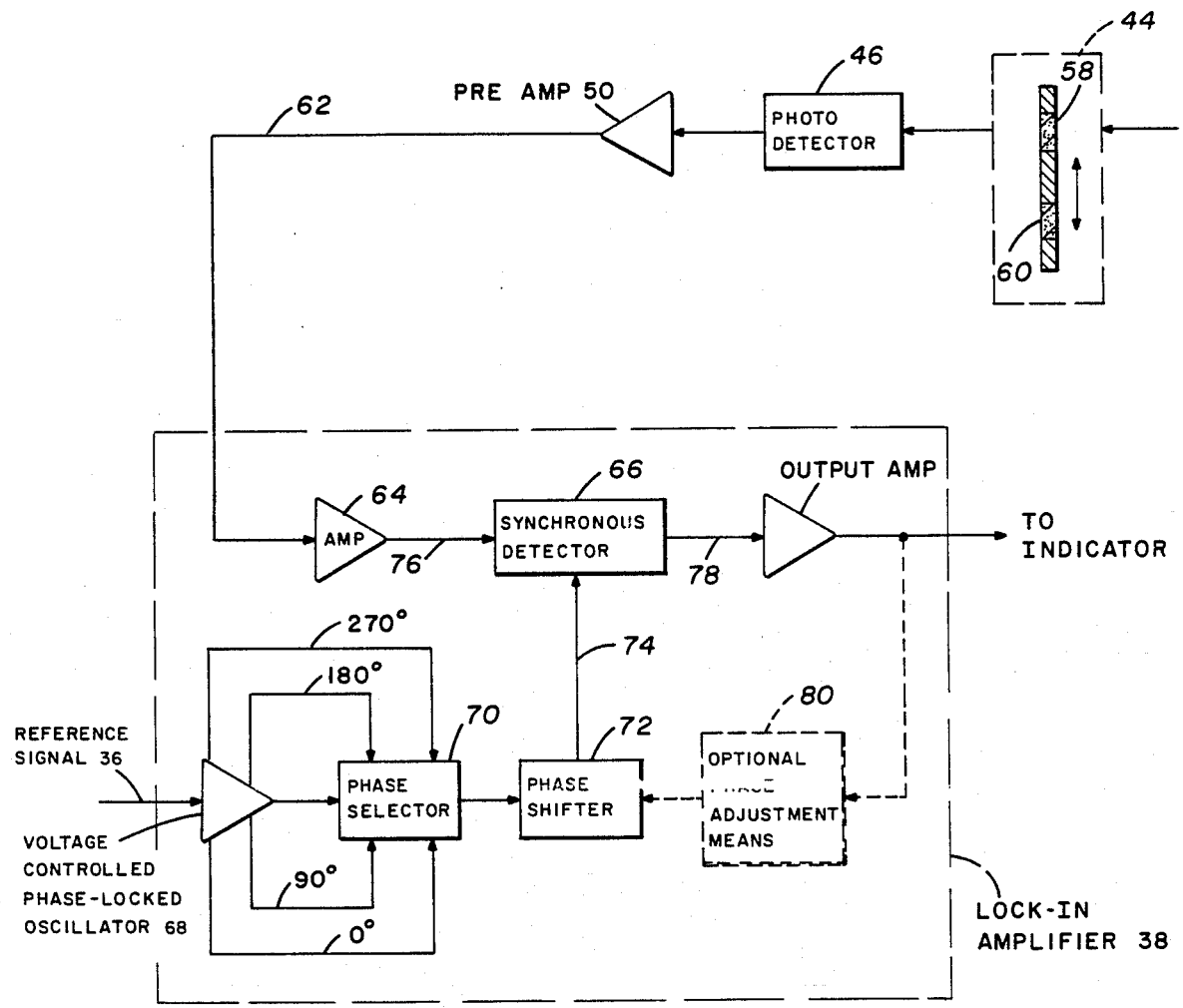
FIG. 5 illustrates, in block diagrammatic form, the improved singlet oxygen monitoring apparatus that utilizes a two wavelength optical comparator.
Figure 6:
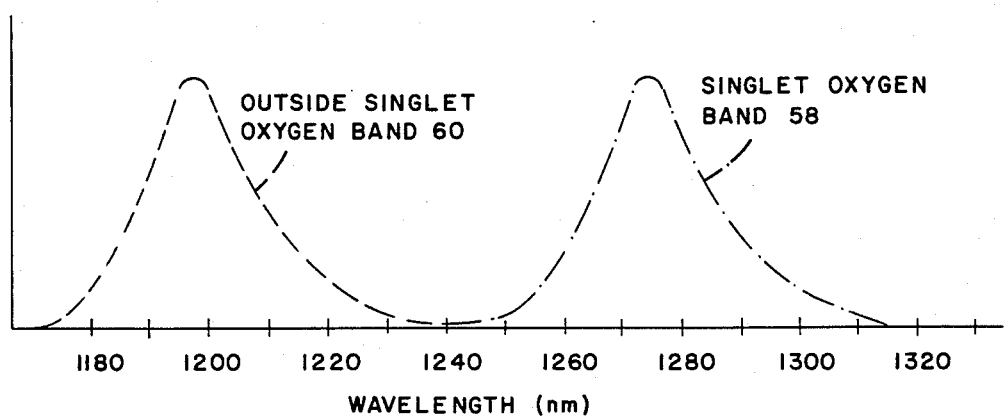
FIG. 6 is a graph showing the optical filter characteristics of the in-band filter and out-of-band filter as taught by the present invention.

Applicant has discovered a method and apparatus for compensating for the electrical phase shift generated in the detector and preamplifier circuits. The invented method and apparatus adjusts the electrical reference signal 36 so that it is coincident with the electrical signal generated by the fluorescence signal component. The improved photodynamic therapy monitoring apparatus is shown in FIG. 5. The apparatus contains the same basic components as described earlier: filter means 44, photodetector 46, preamplifier 50 and lock-in amplifier 38 (alternatively, a synchronous detector or similar circuit can be used). However, the filter means 44 has been modified to include two alternate filters (58, 60). Filter 58 is a narrow band filter that passes light only in the singlet oxygen 1270 nm emission band. Again, emissions in this band is a composite signal containing the fluorescence component as well as the singlet oxygen component. Filter 60 is a narrow band filter that passes light just outside the 1270 nm singlet oxygen emission band. Therefore, the emissions passing through this filter would be almost exclusively the fluorescence component. The general characteristics of filter 58 and 60 are shown in Figure 6 ™ Band width deviations from that shown in FIG. 6 are acceptable as long as one filter contains the singlet oxygen emission and the other is filter is outside the oxygen emission band. The filter outside the singlet oxygen band should be spectrally near the singlet oxygen band so that there will be little or no change in the phase of the fluorescence signal component in these two bands caused by the photodetector. Therefore, filter 58 shall hereinafter be called the "in-band filter"; and, filter 60 should be called the "out-of-band filter".

In operation, light emissions from the biological site is first passed through the "out-of-band filter". The "out-of-band filter" transmits only the infrared fluorescence component. Photodetector 46 and preamplifier 50 generate an electrical signal which is fed to the amplifier 64 and synchronous detector 66 that are associated with the lock-in amplifier 38. The electrical reference signal 36 passes through a voltage control phase-locked oscillator 68, phase selector 70 and phase shifter 72 to the synchronous detector 66. The phase selector is set so that the quadrature component (phase $\phi = -90°$) of the reference signal 36 is input to the phase shifter 72. The phase shifter 72 allows one to add or subtract a small phase shift onto the quadrature component of the reference signal. The synchronous detector provides an output 78 based on the reference signal input and the detector signal input 76. Alternative circuitry can be substituted for the synchronous detector such as a mixer or phase sensitive detector; such alternative circuitry shall be generically called a synchronous detector. Basically, the synchronous detector multiplies the reference signal input with the detector signal input 76. The phase shifter 72 is adjusted until the output of the synchronous detector 66 is zero. The output of the synchronous detector being zero means that the detected signal input 76 is concurrent with the reference signal 74. This means that the electrical signal generated only by the fluorescence emission component is now concurrent with the reference electrical signal 36 and the phase shift added by phase shifter 72 now compensates for the undesirable phase shift discussed earlier. The fluorescence signal component vector is now concurrent with the horizontal axis as shown in FIG. 2, and synchronization adjustment is completed.

To measure the singlet oxygen signal, the "in-band filter" is used to replace the "out-of-band filter" and phase detector 70 and phase shifter 72 are kept at the positions established above. Since the detector phase (quadrature condition) is established, the output from the lock-in amplifier 38 will give a non-zero signal because of the existence of the time-delayed singlet oxygen emission.

This self-referencing two-band comparative method for establishing the zero quadrature condition for the fluorescence only component uniquely enhances the accuracy of the photodynamic therapeutic monitoring system. The two filters could be replaced by a spectrometer which provides the same basic function but would result in greater signal loss. Further, the method can be automated with the use of a phase adjustment means 80 shown in FIG. 5. The phase adjustment means receives an input from the synchronous detector and controls the phase shift added by the phase shifter 72. The phase adjustment means 80 could be a microprocessor control circuit that adjusts the phase shift 72 until the synchronous detector output is zero.

Figure 7:
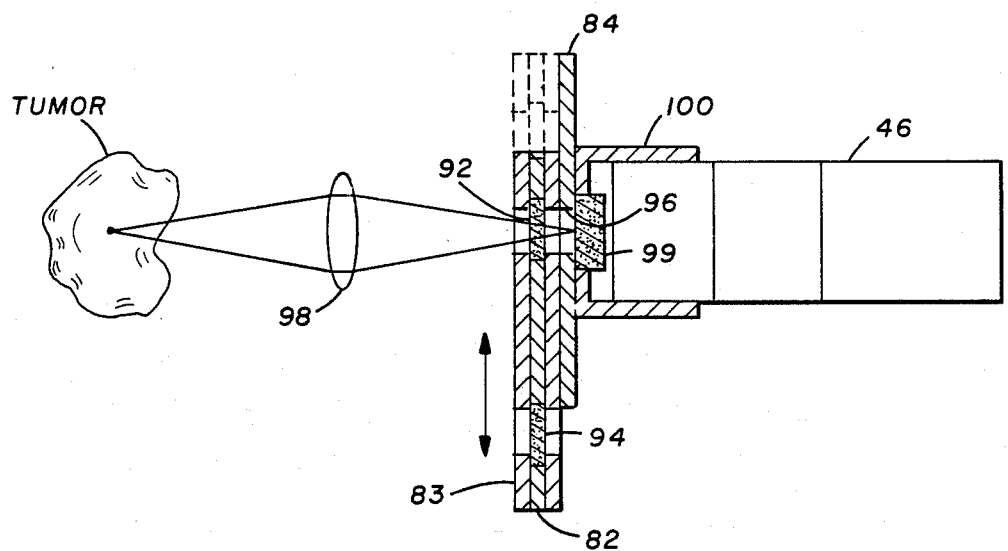
FIG. 7 illustrates, in block diagrammatic form, the two band optical comparator.

FIG. 7 shows a more detailed view of a filter means 44 that provides optimum optical coupling to the detector. A movable filter carriage plate 82 is held firmly between an aperture plate 84 and a front plate 83. the filter carriage plate 82 includes an "out-of-band filter" 92 and an "in-band filter" 94. The filter carriage plate 82 can be moved back and forth (as indicated by the arrows) thus allowing the "out-of-band filter" or "in-band filter" to be positioned in front of the aperture 96. Therefore, light emitted from the biological site will be collected by either a fiberoptic means or a lensing means 98 and will pass either through the "in-band filter" or the "out-of-band filter" and then through aperture 96 and band pass filter 99 (1150–1320 nm) to photodetector 46. A light shield 100 prevents stray light from entering the photodetector.

It is to be understood that it is within the scope of the present invention to use other mechanisms for alternatively placing the "in-band filter" and the "out-of-band filter" in front of the detector aperture. A rotating system as well as the transverse motion system is possible; in addition, an electromechanical mechanism could be used to move the filters in position as well as a manually controlled mechanism. Further, although the above example shows the phase of the reference electrical signal being adjusted to compensate for the undesired electrical phase shift, it is also contemplated that the detected electrical signal could alternatively have a phase shift introduced to it which would compensate for the undesirable electrical phase shift.

Obviously many modifications and variations of the present invention are possible in light of the above teachings. It is therefore to be understood that within the scope of the appended claims the invention may be practiced otherwise than as specifically described.

What is claimed is:

1. An apparatus for detecting singlet oxygen emission produced during photoradiation, comprising:
   an optical excitation means for illuminating a particular portion of a medium containing a photodynamic sensitizer with chopped optical radiation of a wavelength capable of at least causing generation of emission around 1270 nm, wherein said emission includes a first emission component and a second emission component out of phase with said first emission component;

an means for collecting emission from said medium and for sequentially and selectively transmitting a first band of emissions containing a first spectral portion of said emission adjacent to but not including the wavelength of 1270 NM, and then a second band containing a second spectral portion of said emission including said 1270 nm wavelength;

an electro-optical means for detecting emission collected and filtered by said for collecting means, detection of emissions transmitted in said first spectral band producing a first output electrical signal responsive essentially to said the intensity of first portion of said emission, detection of emissions transmitted in said second spectral band producing a second output electrical signal responsive to the intensity of; said second portion of said emissions;

a means for generating an electrical reference signal of the same frequency as said chopped optical excitation radiation, a means for adjusting the phase of said electrical reference signal until it is in phase with said first output electrical signal detected in said first band; and, a signal processing means for separating said second emission component from said second output electrical signal by determining the component of said second output electrical signal in said second band that is about 90° out of phase with said synchronised electrical reference signal, whereby said component of said second output signal is a measure of singlet oxygen emission.

2. The apparatus of claim 1, wherein said means for collecting comprises:
a first filtering means for blocking light outside said first band of emissions;
a second filtering means for blocking light outside said second band of emissions, and,
a means for selectively and sequentially placing said first filtering means and said second filtering means so as to alternatively transmit said first band of emissions or said second band of emissions.

3. The apparatus of claim 1, wherein said electrooptical means includes a preamplifier means for amplifying said detected emissions.

4. The apparatus of claim 1, wherein said signal processing means is a lock-in amplifier receiving as inputs said phase adjusted electrical reference signal and said first or second output electrical signals.

5. A signal processing method for detecting singlet oxygen emission produced during photoradiation, said method comprising the steps of:
illuminating a portion of a medium containing a photodynamic sensitizer with chopped optical radiation having a wavelength capable of at least causing generation of singlet oxygen emission;
collecting luminescence emitted from said medium;
filtering said collected luminescence with a first filter to selectively pass wavelengths in a first spectral band, said first band being spectrally adjacent but not including a wavelength of 1270 nm;
generating an electrical reference signal of the same frequency as said chopped optical radiation;
detecting said emission in said first spectral band and producing a first output electrical signal;
comparing the phase of said first output electrical signal detected in said first band with said electrical reference signal;
adjusting the phase of said reference signal to make it synchronous with said first output electrical signal;
removing said first filter and replacing it with a second filter to selectively pass wavelengths of luminescence in a second spectral band that includes the wavelength of 1270 nm but excludes wavelengths of luminescence outside of the 1270 nm band;
detecting said wavelengths of luminescenc in said second band and producing a composite output signal including a fluorescence emission signal component and a singlet oxygen emission signal component out of phase from said fluorescence emission signal component; and,
processing said composite output signal to separate the singlet oxygen emission signal component from said fluorescence emission signal component based on their relative phase difference, by determining the component of said composite output signal that has a predetermined phase difference from the synchronized reference signal.

6. The method of claim 5, wherein said step of adjusting the phase of said reference signal comprises the steps of:
shifting the phase of said electrical reference signal by 90°, thereby producing a quadrature of said electrical reference signal;
inputting both said quadrature of said electrical reference signal and said first output electrical signal detected in said first band into a synchronous detector; and,
adjusting the phase of said quadrature of said electrical reference signal until the output from said synchronous detector is zero.

7. The method of claim 5, wherein said step of determining involves the step of:
separating a component of said composite electrical signal detected in said second band that is about 90° out of phase from said synchronized electrical reference signal, said separated component representing the singlet oxygen emission signal component.

8. The method of claim 7, wherein said separating step further involves the steps of:
shifting the phase of said synchronized electrical reference signal by 90° thereby generating a quadrature electrical reference signal; and,
inputting said quadrature electrical reference signal and said composite electrical signal detected in said second band to a synchronous detector, the output of said synchronize detector representing the singlet oxygen emission signal.

* * * * *